(12) United States Patent
Harrah et al.

(10) Patent No.: US 10,537,361 B2
(45) Date of Patent: Jan. 21, 2020

(54) ACCESS DEVICE HAVING A FLUID PATHWAY AND METHODS OF USING THE SAME

(71) Applicant: Boston Scientific Limited, Hamilton (BM)

(72) Inventors: Timothy P. Harrah, Cambridge, MA (US); Christopher L. Oskin, Grafton, MA (US); Arpita Banerjee, Bangalore (IN); Abhijit Takale, Maharashtra (IN); Sandesh Gavade, Bangalore (IN); Pavan Misra, Bangalore (IN)

(73) Assignee: Boston Scientific Limited, St. Michael (BB)

( * ) Notice: Subject to any disclaimer, the term of this patent is extended or adjusted under 35 U.S.C. 154(b) by 181 days.

(21) Appl. No.: 15/412,876

(22) Filed: Jan. 23, 2017

(65) Prior Publication Data

US 2017/0215917 A1    Aug. 3, 2017

Related U.S. Application Data

(60) Provisional application No. 62/288,934, filed on Jan. 29, 2016.

(51) Int. Cl.
*A61B 17/02* (2006.01)
*A61B 17/34* (2006.01)
*A61B 17/22* (2006.01)

(52) U.S. Cl.
CPC ...... *A61B 17/3423* (2013.01); *A61B 17/0218* (2013.01); *A61B 17/2202* (2013.01); *A61B 2017/3445* (2013.01); *A61B 2017/3492* (2013.01); *A61B 2217/005* (2013.01)

(58) Field of Classification Search
CPC ............ A61B 17/0218; A61B 17/3423; A61B 17/3417
USPC ....................................................... 600/205
See application file for complete search history.

(56) References Cited

U.S. PATENT DOCUMENTS

| | | | |
|---|---|---|---|
| 4,924,851 A | 5/1990 | Ognier et al. | |
| 2005/0004434 A1 | 1/2005 | Bob et al. | |
| 2005/0192532 A1 | 9/2005 | Kucklick | |
| 2007/0088275 A1* | 4/2007 | Stearns | A61M 1/28 604/164.01 |
| 2007/0173754 A1 | 7/2007 | Kucklick | |
| 2007/0213675 A1 | 9/2007 | Albrecht et al. | |
| 2012/0095291 A1 | 4/2012 | Nakajima | |
| 2013/0178709 A1 | 7/2013 | Suh et al. | |

(Continued)

FOREIGN PATENT DOCUMENTS

WO    2008/030256 A1    3/2008

OTHER PUBLICATIONS

International Search Report and Written Opinion for PCT Patent Application No. PCT/US2017/014700, dated Mar. 28, 2017, 12 pages.

*Primary Examiner* — Si Ming Ku
(74) *Attorney, Agent, or Firm* — Brake Hughes Bellermann LLP (57) ABSTRACT

A medical device includes an elongate member and a port. The elongate member defines a lumen extending from a first end portion of the elongate member to a second end portion of the elongate member. The elongate member defines a helical pathway configured to convey a fluid. The port defines a lumen. The lumen of the port being in fluid communication with the pathway.

20 Claims, 5 Drawing Sheets

(56) References Cited

U.S. PATENT DOCUMENTS

2013/0197592 A1 8/2013 Mafi
2014/0343366 A1 11/2014 Coe et al.

* cited by examiner

FIG. 7

ACCESS DEVICE HAVING A FLUID PATHWAY AND METHODS OF USING THE SAME

CROSS-REFERENCE TO RELATED APPLICATION

This application is a Nonprovisional of, and claims priority to, U.S. Patent Application No. 62/288,934, filed on Jan. 29, 2016, entitled "ACCESS DEVICE HAVING A FLUID PATHWAY AND METHODS OF USING THE SAME", which is incorporated by reference herein in its entirety.

TECHNICAL FIELD

This disclosure relates generally to medical devices and more particularly to medical devices such as access devices or sheaths that include fluid pathways.

BACKGROUND

A variety of medical procedures are performed using an access device or an access sheath. For example, access devices or access sheaths may be used in procedures such as percutaneous nephrolithotomy procedures.

In some procedures that use access devices or access sheaths, it may be difficult for a physician or other medical practitioner to see or visualize the internals of the body of the patient during the procedure. For example, during some procedures bodily tissue or bodily fluid may obscure the vision of the physician or other medical practitioner (for example, while the physician or other medical practitioner is using a scope during a medical procedure).

Accordingly, is may be desirable to provide a device, such as an access device or access sheath, that includes features or components that help increase the visibility that a physician or other medical practitioner may have during the medical procedure.

SUMMARY

According to an aspect, a medical device includes an elongate member and a port. The elongate member defining a lumen extending from a first end portion of the elongate member to a second end portion of the elongate member. The elongate member defining a helical pathway configured to convey a fluid. The port defining a lumen, the lumen of the port being in fluid communication with the pathway.

In some embodiments, the elongate member includes a retention portion and a tubular portion, the retention portion having a size that is larger than the size of the tubular portion. In some embodiments, the elongate member includes a retention portion and a tubular portion, the retention portion being configured to contact a portion of a body of a patient. In some embodiments, the elongate member includes a sidewall, the sidewall defines the lumen of the elongate member, the sidewall defines the helical pathway.

In some embodiments, the elongate member is substantially linear. In some embodiments, the lumen extends substantially linearly from the first end portion of the elongate member to the second end portion of the elongate member. In some embodiments, the port is configured to be coupled to a fluid source.

In some embodiments, the helical pathway is a first pathway, the elongate member defining a second pathway configured to convey fluid. In some embodiments, the helical pathway is a first pathway, the elongate member defining a second pathway configured to convey fluid, the port being a first port, the medical device further comprising a second port, the second port defining a lumen, the lumen of the second port being in fluid communication with the second pathway. In some embodiments, the helical pathway is a first pathway, the elongate member defining a second pathway configured to convey fluid, the port being a first port, the medical device further comprising a second port, the second port defining a lumen, the lumen of the second port being in fluid communication with the second pathway, the second port being configured to be operatively coupled to a fluid source.

In some embodiments, the lumen defined by the elongate member is configured to receive a secondary medical device.

In some embodiments, the first end portion of the elongate member includes an engagement surface, the engagement surface is configured to operatively couple a secondary medical device to the elongate member. In some embodiments, the first end portion of the elongate member includes an engagement surface, the engagement surface is configured to fluidically seal a secondary medical device within the lumen defined by the elongate member.

In some embodiments, the medical device is configured to be inserted into a body of a patient such that at least a portion of the medical device extends from the body of the patient.

In some embodiments, the helical pathway is configured to convey a fluid into a body of a patient.

In another aspect a medical device includes an elongate member, a first port, and a second port. The elongate member having a sidewall, the sidewall defining a lumen extending from a first end portion of the elongate member to a second end portion of the elongate member, the sidewall defining a first pathway configured to convey fluid, the sidewall defining a second pathway configured to convey fluid. The first port defining a lumen, the lumen of the first port being in fluid communication with the first pathway. The second port defining a lumen, the lumen of the second port being in fluid communication with the second pathway.

In some embodiments, the first pathway has a helical shape and extends from the first end portion of the elongate member to the second end portion of the elongate member. In some embodiments, the elongate member is substantially linear and the first pathway is substantially helical. In some embodiments, the lumen is configured to receive a secondary medical device.

In some embodiments, a method includes inserting a medical device into a body of a patient, the medical device includes an elongate member defining a lumen, the elongate member defining a helical pathway; inserting a secondary medical device into the lumen defined by the elongate member of the medical device; and passing a fluid through the helical pathway.

In some embodiments, the inserting a secondary medical device includes operatively coupling the secondary medical device to an engagement surface of the elongate member. In some embodiments, the passing a fluid through the helical pathway includes passing the fluid into the body of the patient, the method further comprising removing at least some of the fluid from the body of the patient.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
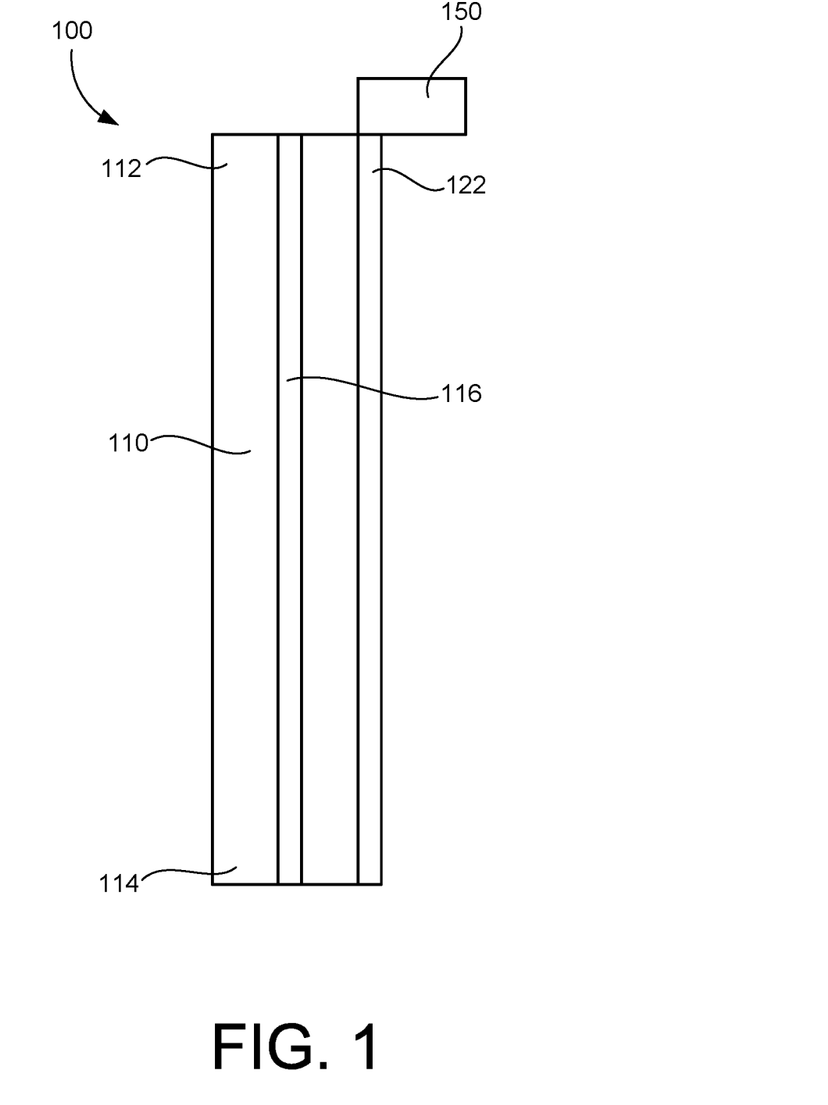
FIG. 1 is a schematic illustration of a medical device according to an embodiment.

FIG. 1 is a schematic illustration of a medical device 100 according to an embodiment of the invention. The medical device 100 may be used in surgical procedures. For example, in some embodiments the medical device 100 may be placed within a body of a patient to create an access or port for further medical procedures. More specifically, in some embodiments, the medical device 100 may be placed within the body of the patient such that a distal end portion of the medical device 100 is disposed within the body of the patient and a proximal end portion of the medical device 100 extends from the body of the patient. In some embodiments, an additional or secondary medical device may be inserted into the body of the patient via the medical device 100 to perform an additional medical procedure.

In the illustrated embodiment, the medical device 100 includes an elongate member 110 and a port 150. The elongate member has a first or proximal end portion 112 and a second or distal end portion 114. The elongate member 110 defines a lumen 116 that extends from the first end portion 112 to the second end portion 114. The lumen 116 is configured to receive a secondary medical device. In some embodiments, the secondary medical device may be used to perform a medical procedure within the body of the patient.

The elongate member 110 also defines a pathway 122. The pathway 122 is configured to convey fluid. For example in some embodiments, the pathway 122 is configured to convey fluid from the first end portion 112 of the elongate member 110 to the second end portion 114 of the elongate member 110. In some embodiments, the pathway 122 is curved or non-linear. In some embodiments, the pathway 122 is helical or partially helical. In some embodiments, the pathway 122 forms loops, rings or circles, as it extends from the first end portion 112 to the second end portion 114.

The port 150 is coupled to the elongate member 110. The port 150 is operatively coupled to the pathway 122. In some embodiments, the port 150 defines a lumen or opening. The lumen or opening of the port 150 is operatively coupled to the pathway 122. In some embodiments, the lumen or opening of the port 150 is operatively coupled (or fluidically coupled) to the pathway 122 such that fluid can pass from the lumen or opening of the port 150 to the pathway 122.

In some embodiments, the port 150 is configured to be coupled to a fluid source. In such embodiments, fluid from the fluid source may be passed from the fluid source, through the port 150, and into the pathway 122. In some embodiments, the port 150 is configured to be coupled to a suction or vacuum device. In such embodiments, fluid may pass from the pathway 122, through the port 150, and to the suction or vacuum device.

Figure 2:
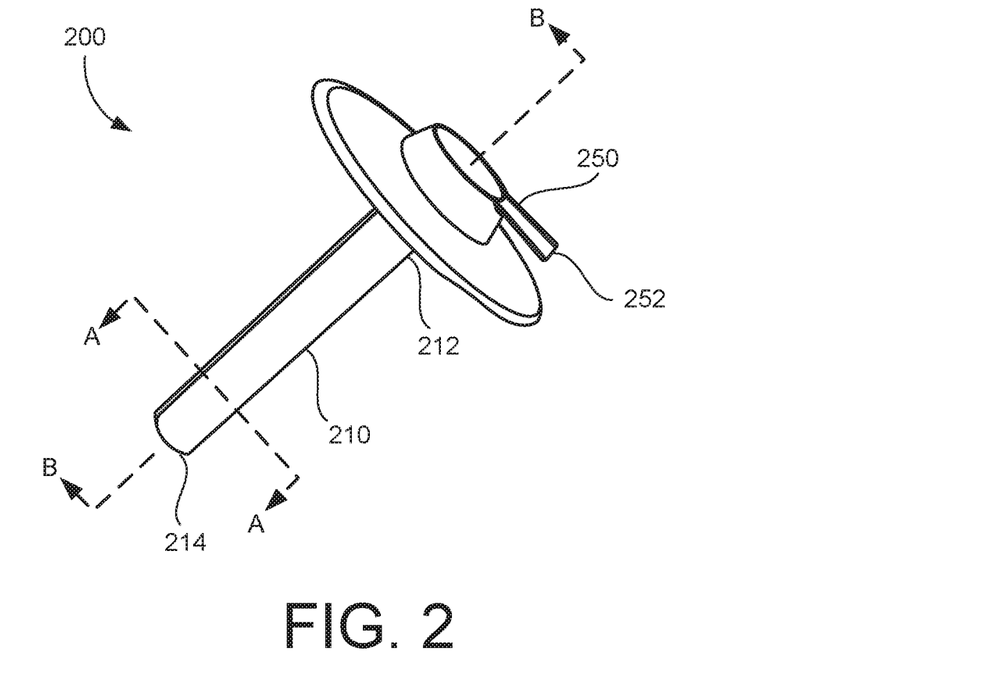
FIG. 2 is a perspective view of a medical device according to an embodiment of the invention.
Figure 3:
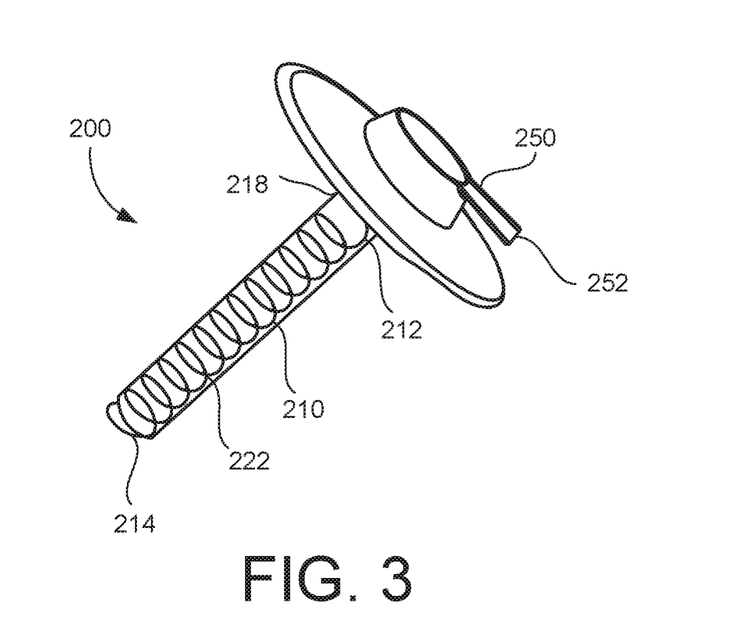
FIG. 3 is a see-through perspective view of the medical device of FIG. 2.
Figures 4, 5:
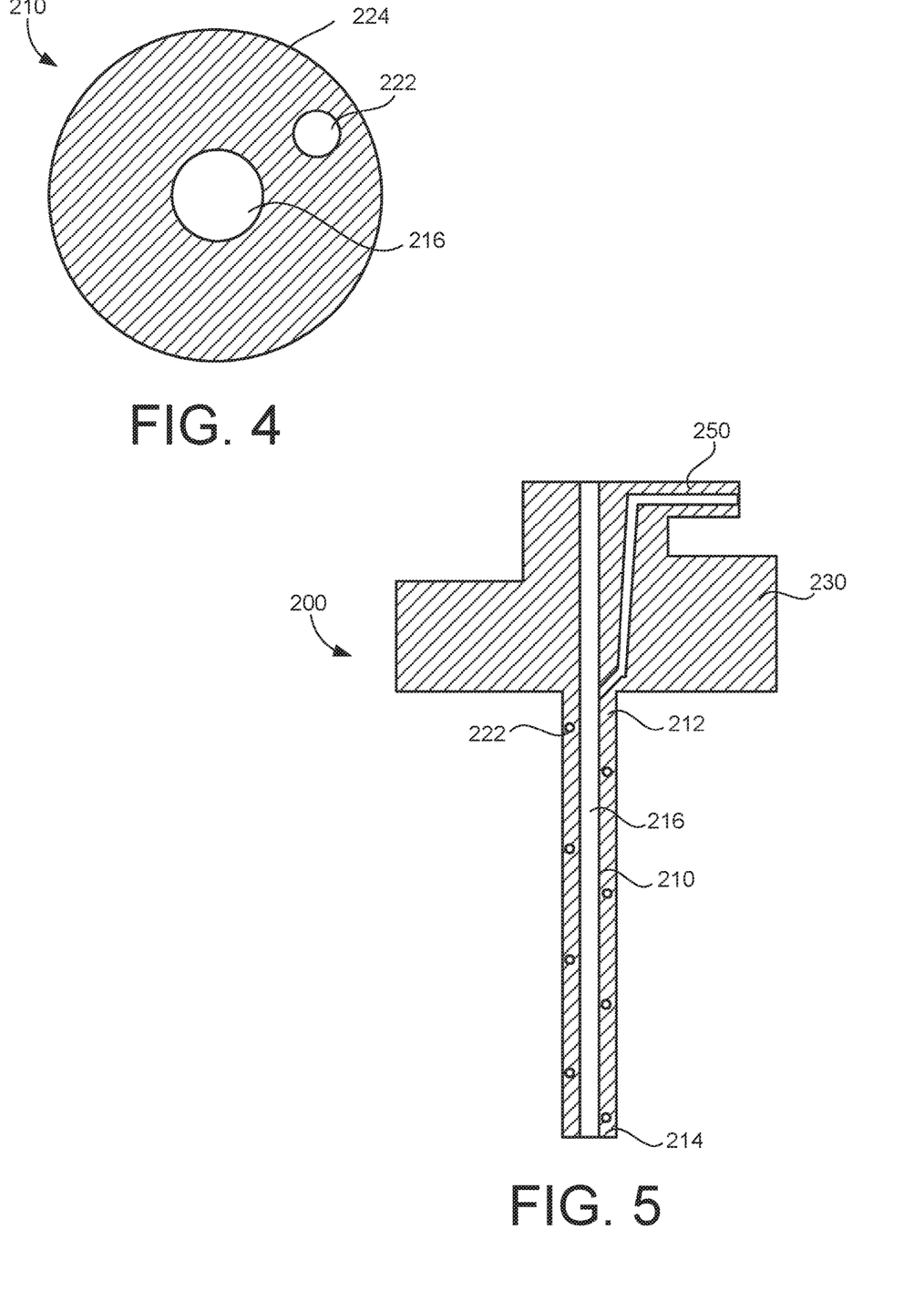
FIG. 4 is a cross-sectional view of the medical device of FIG. 2 taken along line A-A of FIG. 2.
FIG. 5 is a cross-sectional view of the medical device of FIG. 2 taken along line B-B of FIG. 2
Figure 6:
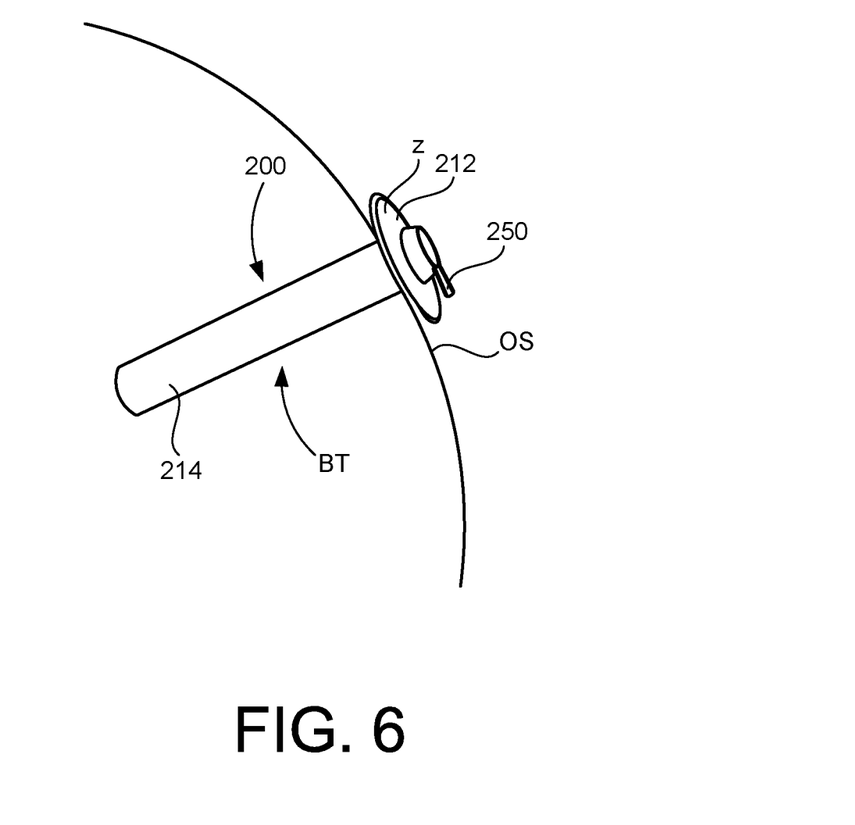
FIG. 6 is a schematic illustration of the medical device of FIG. 2 disposed within a body of a patient.

FIG. 2 is a perspective view of a medical device 200 according to an embodiment of the invention. FIG. 3 is a see-through perspective view of the medical device 200. FIG. 4 is a cross-sectional view of the medical device 200 taken along line A-A of FIG. 2. FIG. 5 is a cross-sectional view of the medical device 200 taken along line B-B of FIG. 2. FIG. 6 is a schematic illustration of the medical device 200 disposed within a body of a patient.

The medical device 200 may be used in surgical procedures. For example, in some embodiments the medical device 200 may be placed within a body of a patient to create an access or port for further medical procedures. More specifically, in some embodiments, the medical device 200 may be placed within the body of the patient such that a distal end portion of the medical device 200 is disposed within the body of the patient and a proximal end portion of the medical device 200 extends from the body of the patient. In some embodiments, an additional or secondary medical device may be inserted into the body of the patient via the medical device 200 to perform an additional medical procedure. For example, in some embodiments, the secondary medical device may be a nephroscope, a lithotripter (such as an ultrasonic lithotripter), a force, a basketing device, a laser fiber, or any other medical device.

In the illustrated embodiment, the medical device 200 includes an elongate member 210 and a port 250. The elongate member 210 has a first or proximal end portion 212 and a second or distal end portion 214. The elongate member 210 defines a lumen 216 that extends from the first end portion 212 to the second end portion 214. The lumen 216 is configured to receive a secondary medical device. In some embodiments, the secondary medical device may be used to perform a medical procedure within the body of the patient. In the illustrated embodiment, the lumen 216 is linear or substantially linear. In other embodiments, the lumen 216 is curved or includes a curved portion.

The elongate member 210 includes an engagement surface 218. In the illustrated embodiment, the engagement surface 218 is located near the first or proximal end portion 212 of the elongate member 210. The engagement surface 218 is configured to contact or engage the secondary medical devices. In some embodiments, the engagement surface 218 is configured to help retain or couple the secondary medical device to the elongate member 210. For example, in some embodiments, the engagement surface 218 is configured to frictionally couple the secondary medical device to the elongate member 210.

In some embodiments, the engagement surface 218 is configured to form a seal around a secondary medical device that is disposed within the lumen 216 of the elongate member 210. For example, in some embodiments, the engagement surface is configured to form a fluid tight seal about or around the secondary medical device. In some embodiments, the engagement surface includes a mechanical or structure portion or feature that engages the secondary medical device to couple the secondary medical device to the elongate member 210 and to form the seal. For example, in some embodiments, a grommet such as a rubber grommet is used to form the fluid tight seal.

The elongate member 210 also defines a pathway 222. The pathway 222 is configured to convey fluid. For example in some embodiments, the pathway 222 is configured to convey fluid from the first end portion 212 of the elongate member 210 to the second end portion 214 of the elongate member 210. In some embodiments, the pathway 222 is curved or non-linear. As best illustrated in FIG. 3, in the illustrated embodiment, the pathway 222 is helical or partially helical. Specifically, the pathway 222 forms loops, rings or circles, as it extends from the first end portion 212 to the second end portion 214.

In the illustrated embodiment, the elongate member 210 includes a sidewall 224. The sidewall 224 defines the pathway 222.

In some embodiments, the helical pathway allows a fluid, such as saline, to be injected or inserted into the body of the patient at a flow rate that is sufficient to allow the physician or other medical practitioner to see a clear endoscopy image. Specifically, a physician or other medical practitioner may adjust the flow rate or increase the flow rate when the vision of the scope is blurred (for example, due to kidney stone dust or fragmentation during a procedure such as a lithotripsy procedure). In some embodiments, the flow rate is about 100 milliliters per minute. In some embodiments, the flow rate is greater than 100 milliliters per minute. In other embodiments, the flow rate is between 50 and 100 milliliters per minute. In some embodiments, the flow rate is not continuous or constant.

The port 250 is coupled to the elongate member 210. The port 250 is operatively coupled to the pathway 222. The port 250 defines a lumen or opening 252. The lumen or opening 252 of the port 250 is operatively coupled to the pathway 222. In some embodiments, the lumen or opening of the port 250 is operatively coupled (or fluidically coupled) to the pathway 222 such that fluid can pass from the lumen or opening of the port 250 to the pathway 222.

In some embodiments, the port 250 is configured to be an inlet and be coupled to a fluid source. In such embodiments, fluid from the fluid source may be passed from the fluid source, through the port 250, and into the pathway 222.

In some embodiments, the port 250 is configured to be an outlet and be coupled to a suction or vacuum device. In such embodiments, fluid may pass from the pathway 222, through the port 250, and to the suction or vacuum device.

In the illustrated embodiment, the elongate member 210 includes a retention portion 230. The retention portion 230 is configured to contact a portion of the a body of the patient to help prevent the entire medical device 200 from being inserted into the body of the patient. For example, in the illustrated embodiment, the retention portion 230 is larger than the remainder of the elongate member 210. The retention portion 230 is configured to contact an outer surface of the body of the patient when the remainder of the distal end portion 214 of the elongate member 210 is disposed within the body of the patient. The contact of the retention portion 230 with the outer surface of the body of the patient may help prevent the entire medical device 200 from being inserted into the body of the patient.

In some embodiments, the elongate member includes a second pathway. In some embodiments, the second pathway may be linear or substantially linear. In some embodiments, the second pathway may be the lumen 216 (as fluid may in some embodiments, be passed between the sidewall that defines the lumen 216 and the secondary medical device). In other embodiments, the second pathway may be defined by the sidewall 224. In some embodiments, one of the pathways may be configured to deliver fluid to the body of the patient and the other of the pathways may be configured to remove fluid from the body of the patient. In some embodiments, fluid removal may be accomplished using a vacuum or other suction type device.

In use, the medical device 200 may be placed within a body of a patient. In some embodiments, the medical device 200 may be placed within the body of the patient such that the distal end portion 214 of the elongate member 210 is disposed within the body of the patient and the proximal end portion 212 of the elongate member 210 extends from the body of the patient (see for example, FIG. 6). As illustrated in FIG. 6, the distal end portion 214 is disposed adjacent bodily tissue and the retention portion may contact or abut an outer surface OS of the body of the patient. A secondary medical device may then be placed into the body of the patient through the lumen 216 defined by the elongate member 210. The port 250 may then be coupled to a fluid source. Fluid may be inserted or injected into the body of the patient through the port 250 and the pathway 222.

The injection of the fluid may provide a clear view (such as clear endoscopy images) to the physician or medical practitioner. The clear view may help facilitate the medical procedure, such as a medical procedure using the secondary medical device.

Figure 7:
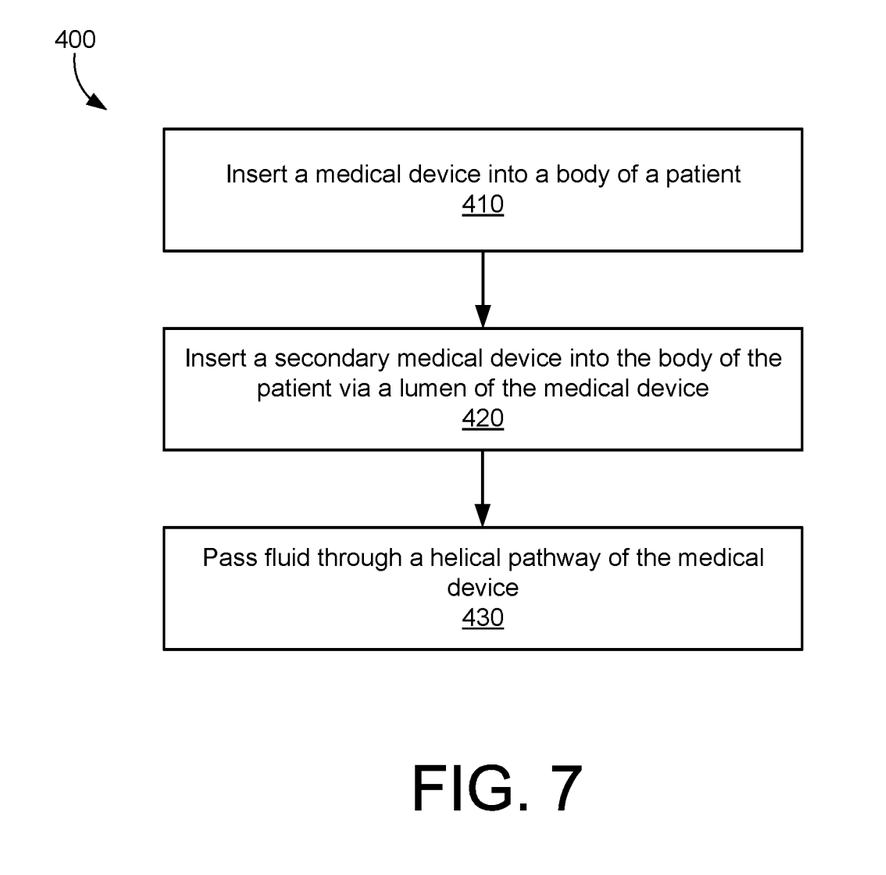
FIG. 7 is a flow chart of a method according to an embodiment.

FIG. 7 is a flow chart of a method 400 according to an embodiment of the invention. At 410, a medical device is inserted into a body of a patient. In some embodiments, the medical device is inserted such that a distal end portion of the device is disposed within the body of the patient and a proximal end portion extends from the body of the patient.

At 420, a secondary medical device is inserted into the body of the patient. In some embodiments, the secondary medical device is inserted into the body of the patient via a lumen defined by the medical device (such as a lumen defined by an elongate member of the medical device).

At 430, fluid is passed or injected into the body of the patient via a helical pathway defined by the medical device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
an elongate member including a sidewall, the sidewall defines a lumen extending from a first end portion of the elongate member to a second end portion of the elongate member, the elongate member defining a helical pathway including a plurality of loops in the sidewall and configured to convey a fluid, the plurality of loops being entirely within a thickness of the sidewall; and
a port, the port defining a lumen, the lumen of the port being in fluid communication with the pathway.

2. The medical device of claim 1, wherein the elongate member includes a retention portion and a tubular portion, the retention portion having a size that is larger than the size of the tubular portion.

3. The medical device of claim 1, wherein the elongate member includes a retention portion and a tubular portion, the retention portion being configured to contact a portion of a body of a patient.

4. The medical device of claim 1, wherein the elongate member is substantially linear.

5. The medical device of claim 1, wherein the lumen extends substantially linearly from the first end portion of the elongate member to the second end portion of the elongate member.

6. The medical device of claim 1, wherein the port is configured to be coupled to a fluid source.

7. The medical device of claim 1, wherein the helical pathway is a first pathway, the elongate member defining a second pathway configured to convey fluid.

8. The medical device of claim 1, wherein the helical pathway is a first pathway, the elongate member defining a second pathway configured to convey fluid, the port being a first port, the medical device further comprising:
a second port, the second port defining a lumen, the lumen of the second port being in fluid communication with the second pathway.

9. The medical device of claim 1, wherein the helical pathway is a first pathway, the elongate member defining a second pathway configured to convey fluid, the port being a first port, the medical device further comprising:
a second port, the second port defining a lumen, the lumen of the second port being in fluid communication with the second pathway, the second port being configured to be operatively coupled to a fluid source.

10. The medical device of claim 1, wherein the lumen defined by the elongate member is configured to receive a secondary medical device.

11. The medical device of claim 1, wherein the first end portion of the elongate member includes an engagement surface, the engagement surface is configured to operatively couple a secondary medical device to the elongate member.

12. The medical device of claim 1, wherein the first end portion of the elongate member includes an engagement surface, the engagement surface is configured to fluidically seal a secondary medical device within the lumen defined by the elongate member.

13. The medical device of claim 1, wherein the sidewall includes a first sidewall portion and a second sidewall portion, the thickness of the sidewall being defined between the first sidewall portion and the second sidewall portion.

14. A medical device, comprising:
an elongate member having a sidewall, the sidewall defining a lumen extending from a first end portion of the elongate member to a second end portion of the elongate member, the sidewall defining a first pathway configured to convey fluid, the sidewall defining a second pathway configured to convey fluid, at least one of the first pathway or the second pathway including a plurality of loops in the sidewall, the plurality of loops being disposed entirely within a thickness of the sidewall;
a first port, the first port defining a lumen, the lumen of the first port being in fluid communication with the first pathway;
a second port, the second port defining a lumen, the lumen of the second port being in fluid communication with the second pathway.

15. The medical device of claim 14, wherein the first pathway is a helical shape and extends from the first end portion of the elongate member to the second end portion of the elongate member.

16. The medical device of claim 14, wherein the elongate member is substantially linear and the first pathway is substantially helical.

17. The medical device of claim 14, wherein the lumen is configured to receive a secondary medical device.

18. A method comprising:
inserting a medical device into a body of a patient, the medical device includes an elongate member including a sidewall, the sidewall defining a lumen, the elongate member defining a helical pathway including a plurality of loops in the sidewall, the plurality of loops being entirely within a thickness of the sidewall;
inserting a secondary medical device into the lumen defined by the elongate member of the medical device; and
passing a fluid through the helical pathway.

19. The method of claim 18, wherein the inserting a secondary medical device includes operatively coupling the secondary medical device to an engagement surface of the elongate member.

20. The method of claim 18, wherein the passing a fluid through the helical pathway includes passing the fluid into the body of the patient, the method further comprising:
removing at least some of the fluid from the body of the patient.

* * * * *